US010016624B2

(12) United States Patent
Yoon et al.

(10) Patent No.: US 10,016,624 B2
(45) Date of Patent: Jul. 10, 2018

(54) RADIATION TREATMENT COLLIMATOR HAVING MULTILAYERED LINKAGE STRUCTURE

(71) Applicant: THE CATHOLIC UNIVERSITY OF KOREA INDUSTRY-ACADEMIC COOPERATION FOUNDATION, Seoul (KR)

(72) Inventors: Do Kun Yoon, Gyeonggi-do (KR); Joo Young Jung, Busan (KR); Tae Suk Suh, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 210 days.

(21) Appl. No.: 14/894,219

(22) PCT Filed: Aug. 5, 2013

(86) PCT No.: PCT/KR2013/007029
§ 371 (c)(1),
(2) Date: Nov. 25, 2015

(87) PCT Pub. No.: WO2014/193032
PCT Pub. Date: Dec. 4, 2014

(65) Prior Publication Data
US 2016/0101296 A1 Apr. 14, 2016

(30) Foreign Application Priority Data

May 30, 2013 (KR) .................. 10-2013-0062062

(51) Int. Cl.
*A61N 5/10* (2006.01)
*G21K 1/04* (2006.01)

(52) U.S. Cl.
CPC ............ *A61N 5/1045* (2013.01); *A61N 5/10* (2013.01); *G21K 1/046* (2013.01);
(Continued)

(58) Field of Classification Search
CPC .. G21K 1/046; A61N 5/10; A61N 2005/1094; A61N 5/1045; A61N 2005/1074; A61N 2005/1095
See application file for complete search history.

(56) References Cited

U.S. PATENT DOCUMENTS

| 5,396,304 A | * | 3/1995 | Salerno | ................. A61B 3/113 257/E27.111 |
| 5,847,939 A | * | 12/1998 | Cotton | ................. H01H 9/0044 200/11 TC |

(Continued)

FOREIGN PATENT DOCUMENTS

| KR | 10-2012-0002359 A | | 1/2012 |
| KR | 10-2013-0039616 A | | 4/2013 |
| KR | 20130039616 A | * | 4/2013 |

OTHER PUBLICATIONS

International Search Report issued in connection with PCT/KR2013/007029.

*Primary Examiner* — Christine H Matthews
*Assistant Examiner* — Joshua D Lannu
(74) *Attorney, Agent, or Firm* — Akerman LLP

(57) ABSTRACT

A radiation treatment collimator having a multilayered linkage structure, the collimator providing various shapes of spaces to form an irradiation area transmitting radioactive rays therethrough, the collimator comprising: a fixed frame disposed on a plate; multiple pixel board layers fixedly stacked at predetermined intervals on top of each other inside the fixed frame, each pixel board layer being configured in a lattice form and having pixel covers disposed correspondingly to the respective lattices in such a manner (Continued)

as to be open and closed individually; control units disposed on both sides of the fixed frame to individually control the operations of the pixel covers of the pixel board layers; and power source units disposed on the front and rear sides of the fixed frame to supply the pixel board layers with operating power.

5 Claims, 3 Drawing Sheets

(52) U.S. Cl.
CPC ................. *A61N 2005/1074* (2013.01); *A61N 2005/1094* (2013.01); *A61N 2005/1095* (2013.01)

(56) References Cited

U.S. PATENT DOCUMENTS

| | | |
|---|---|---|
| 2004/0104350 A1 | 6/2004 | Tsuchiya et al. |
| 2008/0165922 A1* | 7/2008 | Yanoff .................. A61B 6/032 378/19 |
| 2012/0039446 A1 | 2/2012 | Cui et al. |

* cited by examiner

RADIATION TREATMENT COLLIMATOR HAVING MULTILAYERED LINKAGE STRUCTURE

This application is a national phase of PCT/KR2013/007029, filed Aug. 5, 2013, and claims priority to KR 10-2013-0062062, filed May 30, 2013, the entire contents of both of which are hereby incorporated by reference.

TECHNICAL FIELD

The present invention relates to a radiation treatment collimator having a multilayered linkage structure, and more particularly, to a radiation treatment collimator having a multilayered linkage structure wherein each of multilayered pixel board layers includes pixel boards structured in a lattice form and pixel covers corresponding to the lattices of the respective pixel boards having the lattice structures, so that the pixel covers are individually open and closed to form a radiation transmission area through which radiation is transmitted.

BACKGROUND ART

In the treatment of radioactive rays like X rays or gamma rays, a collimator is used to adjust the doses of radiation. A representative example of such conventional collimators is a multileaf collimator configured to have multiple leaves moved individually to maintain or convert a specific shape of space corresponding to an area through which the dose of radiation is transmitted, so that the multileaf collimator makes use of a driving system that transmits the dose of radiation through the movement of multiple leaves by time.

The conventional multileaf collimator is necessarily attached to almost all kinds of radiation treatment machines used currently in radiation oncology, but inconveniently, the multiple leaves should be directly moved and individually operated. Most of the multileaf collimators are expensive and hard to be manufactured, and when the multiple leaves are used in the state of being attached to the radiation treatment machine, further, they are moved momentarily to maintain the shape of space only at the same position, without being changed in position.

Accordingly, there is a define need for the development of a new radiation treatment collimator capable of being made at a lower manufacturing cost than that in the existing multileaf collimators, while having the same treatment performance, and further, capable of providing high performance in the formation of complicated areas for the dose of radiation or in the control of the intensity of short or irregular doses of radiation.

DISCLOSURE

Technical Problem

Accordingly, the present invention has been made in view of the above-mentioned problems occurring in the prior art, and it is an object of the present invention to provide a radiation treatment collimator having a multilayered linkage structure that is configured to introduce the concepts of the pixels used in image, without having the existing leaf system, and further to introduce the multilayered linkage structure, so that when a radiation dose is transmitted to a target, a complicated shape like a shape of root or donut is formed in a unit of a pixel made by pixel covers arranged in a lattice form on pixel boards formed on each of multilayered pixel board layers, and as the pixel covers of the respective pixel board layers are individually open and closed, accordingly, a radiation transmission area through which radiation is transmitted is in real time maintained in shape, while the intensity of radiation is being at the same time controlled.

Technical Solution

To accomplish the above-mentioned object, according to the present invention, there is provided a radiation treatment collimator having a multilayered linkage structure, the collimator providing various shapes of spaces to form an irradiation area transmitting radioactive rays therethrough, the collimator including: a fixed frame disposed on a plate; multiple pixel board layers fixedly stacked at predetermined intervals on top of each other inside the fixed frame, each pixel board layer being configured in a lattice form and having pixel covers disposed correspondingly to the respective lattices in such a manner as to be open and closed individually; control units disposed on both sides of the fixed frame to individually control the operations of the pixel covers of the pixel board layers; and power source units disposed on the front and rear sides of the fixed frame to supply the pixel board layers with operating power.

According to the present invention, preferably, each pixel board layer is configured to have the pixel covers connected at one side thereof to hinge shafts each having a micro motor embedded thereinto in such a manner as to be connected serially to each other to a shape of a board to form one pixel board, and to have one pixel board connected to other pixel boards in a width direction thereof, and the pixel covers connected to the hinge shafts rotating through the driving of the micro motors are open and closed individually under the control of the control units.

According to the present invention, preferably, the opening/closing angle of each pixel cover of the pixel board layers is in the range of 0 to 90°.

According to the present invention, preferably, the control units control each pixel cover of the pixel board layers in association with a radiation treatment machine.

According to the present invention, preferably, the radiation treatment collimator further comprises a protection cover located around each control unit.

Advantageous Effects

According to the present invention, the radiation treatment collimator having a multilayered linkage structure can be made at a lower manufacturing cost and with higher performance when compared with the existing multileaf collimators, while having the same treatment effects.

Further, the radiation treatment collimator according to the present invention can form the irradiation area through which radiation is transmitted by means of the opening and closing of the pixel covers formed as a unit of a pixel, unlike the conventional multileaf collimators, thus allowing the shape of the irradiation area and the intensity of radiation to be in real time changed and controlled.

Furthermore, the radiation treatment collimator according to the present invention can build a pilot line at a lower cost than that in the conventional multileaf collimator and further can construct an independent production line as new radiation treatment products, thus expecting enormous gains therefrom.

BEST MODE FOR INVENTION

Hereinafter, an explanation on a radiation treatment collimator having a multilayered linkage structure according to the present invention will be in detail given with reference to the attached drawing. Before the present invention is disclosed and described, however, it is to be understood that the disclosed embodiments are merely exemplary of the invention, which can be embodied in various forms.

According to the present invention, a radiation treatment collimator having a multilayered linkage structure has a radiation shielding system different from the conventional multileaf collimator. The conventional multileaf collimator forms a linear type irradiation area, but the radiation treatment collimator according to the present invention forms a pixel, that is, dot type irradiation area. According to the present invention, pixel covers disposed on each of multilayered pixel board layers are open and closed individually on a radiation transmission area, so that radiation is transmitted through the radiation transmission area, thus allowing the intensity of the radiation to be controlled.

Accordingly, the pixel covers disposed on the pixel board layers are just open and closed individually in the state where the pixel board layers are fixed, unlike the conventional multileaf collimator wherein the leaves are momentarily moved, thus achieving the control of the intensity of radiation in a stable manner.

MODE FOR INVENTION

Now, the radiation treatment collimator having a multilayered linkage structure according to the present invention will be in detail explained with reference to the attached drawing.

Figure 1:
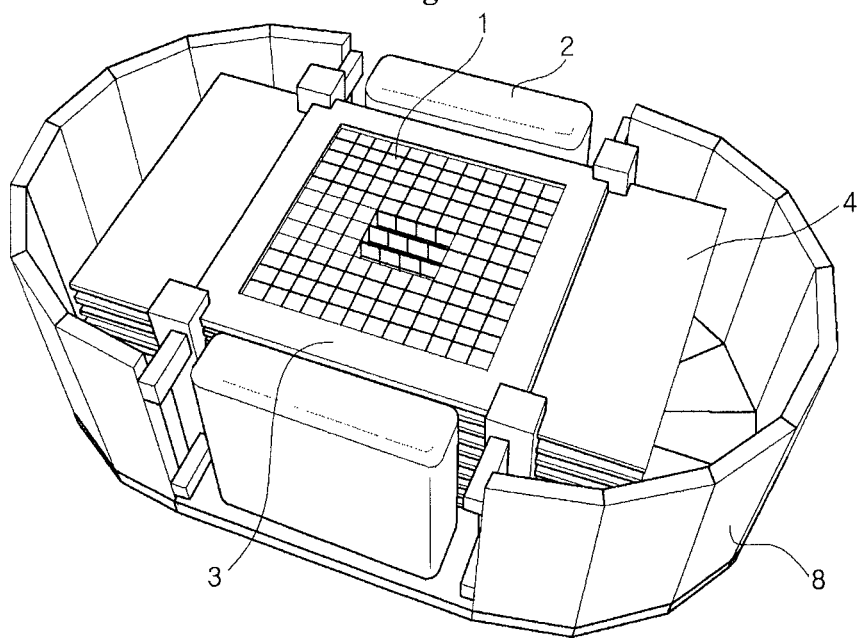
FIG. 1 is a perspective view showing a radiation treatment collimator having a multilayered linkage structure according to the present invention.
Figure 2:
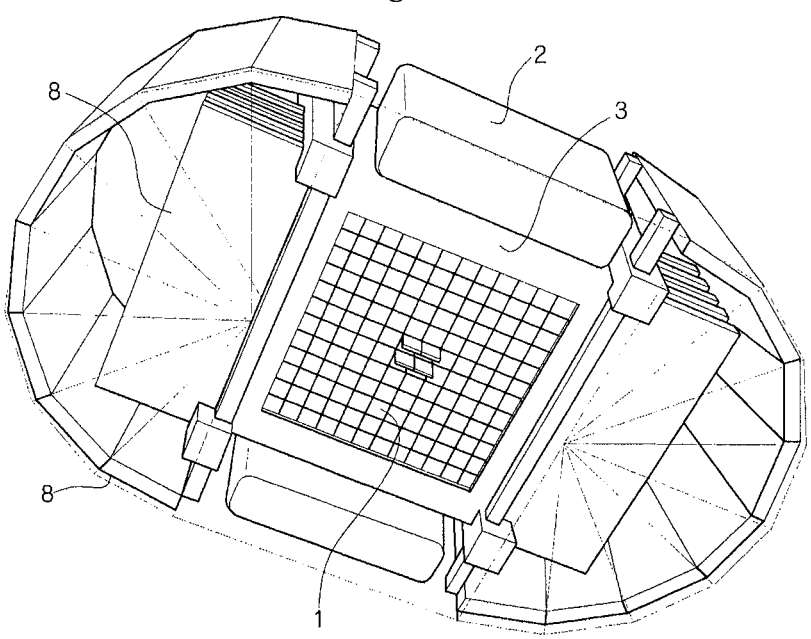
FIG. 2 is a bottom perspective view showing the radiation treatment collimator having a multilayered linkage structure according to the present invention.

FIG. 1 is a perspective view showing a radiation treatment collimator having a multilayered linkage structure according to the present invention, and FIG. 2 is a bottom perspective view showing the radiation treatment collimator having a multilayered linkage structure according to the present invention.

As shown in FIGS. 1 and 2, a radiation treatment collimator having a multilayered linkage structure according to the present invention basically includes a fixed frame 3, pixel board layers 1, control units 4, and power source units 2.

The fixed frame 3 has a shape of a square, in which a plurality of pixel board layers 1 is fixedly laminated at predetermined intervals on top of each other.

Figure 3:
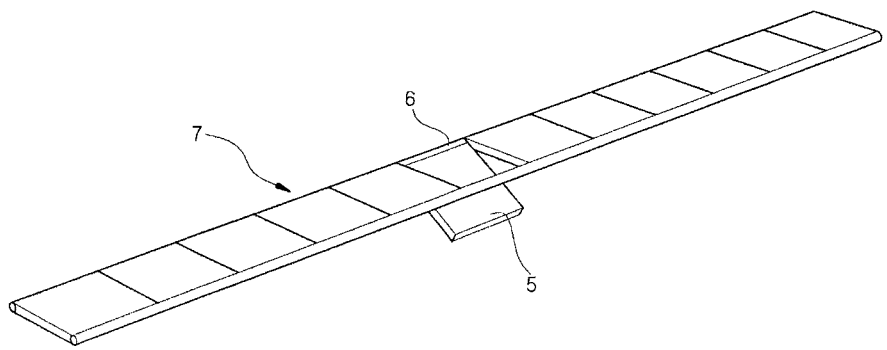
FIG. 3 is a perspective view showing a pixel board of each pixel board layer in the radiation treatment collimator having a multilayered linkage structure according to the present invention.

Each of the square-shaped pixel board layers 1 is configured in a lattice form of a pixel unit, and, as shown in FIG. 3, it includes a plurality of pixel covers 5 disposed on respective pixels corresponding to the lattices, hinge shafts 6 connected to one side of the pixel covers 5, and pixel boards 7 each formed by serially connecting the pixel covers 5 connected to the hinge shafts 6 with each other, whereby the pixel boards 7 are connected in a width direction with each other to form each square-shaped pixel board layer 1. Each hinge shaft 6 has a micro motor embedded thereinto, and through the activation of the micro motor, it rotates, thus allowing the corresponding pixel cover 5 to be open and closed.

The number of pixel board layers 1 as shown in the drawings is just tens or more, but preferably, 52 pixel board layers 1 are multilayered to a height of about 26 cm. The pixel covers 5 are made of tungsten alloys capable of shielding radioactive rays.

The control units 4 are located on both sides of the fixed frame 3 and have logic circuits and driving circuits embedded thereinto, and through the operations of the logic circuits and driving circuits, the micro motors are driven, thus rotating the hinge shafts 6 connected to the micro motors, so that the respective pixel covers 5 of the pixel board layers 1 are open and closed individually. The control units 4 are connected softwarily to a computer circuit driving a radiation treatment machine and control the respective pixel covers 5 individually in association with the driving of the radiation treatment machine.

Accordingly, as shown in FIG. 1, some of the pixel covers 5 located at the center of the upper pixel board layers 1 are open, and even if not shown, the pixel covers 5 of the middle pixel board layers 1 located correspondingly to the open pixel covers 5 of the upper pixel board layers 1 are open. Further, as shown in FIG. 2, some of the pixel covers 5 located at the center of the lower pixel board layers 1 are open. As a result, radioactive rays are irradiated linearly from the upper pixel board layers 1 to the lower pixel board layers 1, thus appropriately forming a space of a hole as a radiation transmission area, through which the radioactive rays are transmitted. In this case, the opening/closing angle of each pixel cover 5 is desirably in the range of 0 to 90° in the pixel unit. If necessary, preferably, each pixel cover 5 is open to 90% through which the radioactive rays are completely passed.

The power source units 2 are disposed on the front and rear sides of the fixed frame 3 to supply power required for operating the micro motors, thus allowing the pixel covers 5 to be open and closed.

While the fixed frame 3 and the pixel board layers 1 are being located on a plate, on the other hand, protection covers 8 are located on the plate in such a manner as to surround the edges of the control units 4, thus protecting the control units 4 disposed on both sides of the fixed frame 3.

Next, an explanation on the pixel covers 5 constituting the radiation transmission area, through which the radiation is transmitted from the radiation treatment collimator according to the present invention, will be given.

Figure 4:
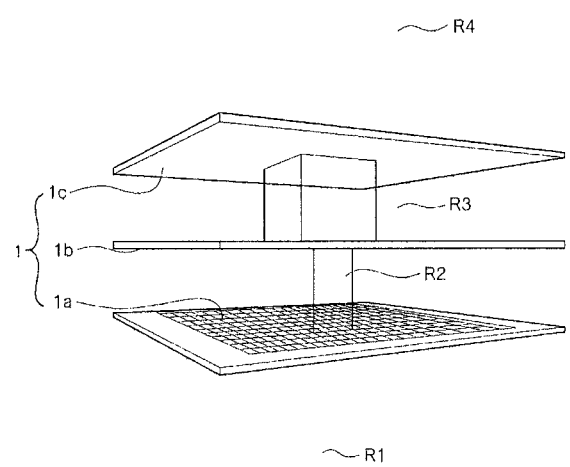
FIG. 4 is a perspective view showing the control of the intensity of radiation by means of the radiation treatment collimator having a multilayered linkage structure according to the present invention.
Figure 5:
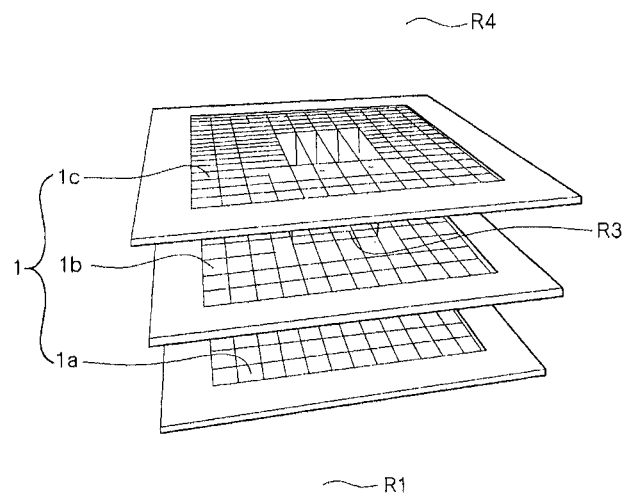
FIG. 5 is a perspective view showing the control of the intensity of radiation in another direction by means of the radiation treatment collimator having a multilayered linkage structure according to the present invention.

FIG. 4 is a perspective view showing the control of the intensity of radiation by means of the radiation treatment collimator having a multilayered linkage structure according to the present invention, and FIG. 5 is a perspective view showing the control of the intensity of radiation in another direction by means of the radiation treatment collimator having a multilayered linkage structure according to the present invention.

As shown in FIGS. 4 and 5, the number of pixel covers 5 open becomes decreased from the center of the uppermost pixel board layer 1c of the pixel board layers 1 toward the center of the lowermost pixel board layer 1a, thus making the space of the radiation transmission area gradually decreased. As the radioactive rays are passed through the respective pixel board layers 1, accordingly, the intensity of the radioactive rays are gradually reduced to high intensity R4, intermediate intensity R3, and low intensity R2, and finally decreased to the lowest intensity R1 when irradiated.

Through the real time individual opening and closing operations of the pixel covers 5 of each pixel board layer 1 by means of the control of the control units 4 operated in association with the computer circuit driving the radiation treatment machine, the spaces of the radiation transmission area are variously formed, and accordingly, the radioactive rays are transmitted only through the open spaces, thus controlling the intensity of the radiation.

Figure 6:
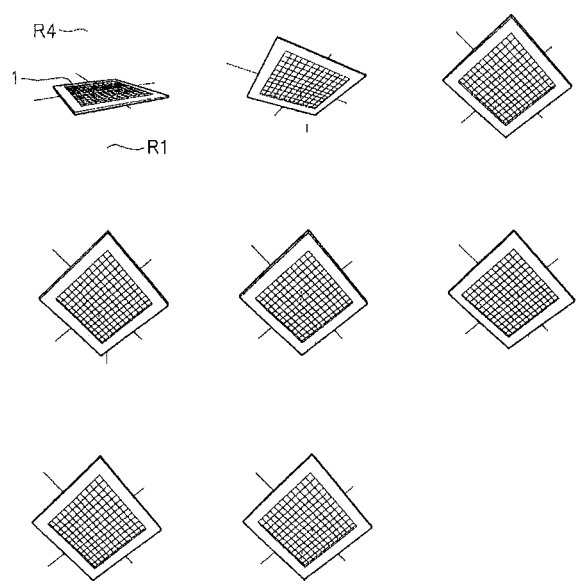
FIG. 6 is a perspective view showing a variety of radiation transmission areas formed in real time by means of the radiation treatment collimator having a multilayered linkage structure according to the present invention.

FIG. 6 is a perspective view showing a variety of radiation transmission areas formed in real time by means of the radiation treatment collimator having a multilayered linkage structure according to the present invention.

As shown in FIG. 6, the radiation treatment collimator according to the present invention is capable of controlling the intensity of the radiation from the high intensity R4 to the lowest intensity R1 and moving the radiation transmission area in real time. In the state where the shape of the space is maintained, that is, if it is desired to change the shape of the space in real time, the positions at which the pixel covers 5 of each pixel board layer 1 are open are momentarily moved under the control of the control units 4, so that the position of the space as well as the shape of the space are changed and continuously maintained, thus allowing the radiation treatment collimator of the present invention to be applicable to real time radiation treatment.

As mentioned above, the radiation treatment collimator according to the present invention is configured to introduce the concepts of the pixels used in image, without having the existing leaf system, and further to introduce the multilayered linkage structure. When a radiation dose is transmitted to a target, accordingly, a complicated shape like a shape of root or donut is formed in the pixel unit through the individual opening and closing of the pixel covers. At the same time, the intensity of radiation is controlled for the shape of the space in real time maintained in accordance with the opening/closing of the pixel covers of the multilayered pixel board layers.

While the present invention has been described with reference to the particular illustrative embodiments, it is not to be restricted by the embodiment but only by the appended claims. It is to be appreciated that those skilled in the art can change or modify the embodiments without departing from the scope and spirit of the present invention.

INDUSTRIAL APPLICABILITY

According to the present invention, the radiation treatment collimator having the multilayered linkage structure is made with new technology and idea at a lower manufacturing cost and with higher performance when compared with the existing multileaf collimator, while having the same treatment effects.

Further, the radiation treatment collimator according to the present invention forms the radiation transmission area, through which radiation is transmitted, by means of the opening and closing of the pixel covers as a unit of a pixel, unlike the conventional multileaf collimator, thus allowing the shape of the radiation transmission area and the intensity of radiation to be in real time changed and controlled.

Furthermore, the radiation treatment collimator according to the present invention builds a pilot line at a lower cost than that in the conventional multileaf collimator and further constructs an independent production line as new radiation treatment products, thus expecting enormous gains therefrom.

The invention claimed is:

1. A radiation treatment collimator having a multilayered linkage structure, the collimator providing various shapes of spaces to form an irradiation area transmitting radioactive rays therethrough, the collimator comprising:
    a fixed frame disposed on a plate;
    multiple pixel board layers fixedly stacked at predetermined intervals on top of each other inside the fixed frame, each pixel board layer being configured in a lattice form and having pixel covers disposed correspondingly to respective lattices in such a manner as to be open and closed individually;
    control units, comprising circuitry, disposed on both sides of the fixed frame to individually control operations of the pixel covers of the pixel board layers; and
    power source units disposed on front and rear sides of the fixed frame to supply the pixel board layers with operating power.

2. The radiation treatment collimator according to claim 1, wherein each pixel board layer is configured to have the pixel covers connected at one side thereof to hinge shafts each having a micro motor embedded thereinto in such a manner as to be connected serially to each other to a shape of a board to form one pixel board, and to have one pixel board connected to other pixel boards in a width direction thereof, the pixel covers connected to the hinge shafts are open and closed individually under the control of the control units, and the hinge shafts rotate through driving of the micro motors.

3. The radiation treatment collimator according to claim 2, wherein an opening/closing angle of each pixel cover of the pixel board layers is in the range of 0 to 90°.

4. The radiation treatment collimator according to claim 1, wherein the control units control each pixel cover of the pixel board layers in association with a radiation treatment machine.

5. The radiation treatment collimator according to claim 1, further comprising a protection cover located around each control unit.

* * * * *